United States Patent

Moll et al.

Patent Number: 5,839,487
Date of Patent: Nov. 24, 1998

[54] SAFETY FILLING DEVICE FOR ANESTHETIC EVAPORATORS

[75] Inventors: Stefan Moll; Uwe Bausch; Stefan Linke; Dirk-Stefan Reichert; Karl-Ludwig Gippert, all of Lübeck; Wolfgang Falb, Krummesse, all of Germany

[73] Assignee: Drägerwerk Aktiengesellschaft, Lübeck, Germany

[21] Appl. No.: 734,829

[22] Filed: Oct. 22, 1996

[30] Foreign Application Priority Data

Apr. 6, 1996 [DE] Germany .................. 196 13 827.2

[51] Int. Cl.⁶ .................................................. A61M 16/18
[52] U.S. Cl. ........................... 141/326; 141/18; 141/392; 220/331
[58] Field of Search ................. 141/18, 326, 392; 128/200.24, 203.12; 220/325, 327, 329, 331, 335

[56] References Cited

U.S. PATENT DOCUMENTS

| | | |
|---|---|---|
| 310,741 | 1/1885 | Stevenson .................... 220/329 |
| 3,349,947 | 10/1967 | Zumwalt ...................... 220/327 |
| 4,286,727 | 9/1981 | Limoncelli .................... 220/331 |
| 4,346,701 | 8/1982 | Richards ................... 128/200.14 |
| 4,576,308 | 3/1986 | Sullivan ....................... 220/327 |
| 5,287,898 | 2/1994 | Falb et al. ..................... 141/329 |
| 5,398,737 | 3/1995 | Heinonen et al. ............. 141/285 |

FOREIGN PATENT DOCUMENTS 41 06 906 A1  9/1992  Germany .

*Primary Examiner*—J. Casimer Jacyna
*Attorney, Agent, or Firm*—McGlew and Tuttle

[57] ABSTRACT

A safety filling device for filling a liquid anesthetic into a reservoir of an anesthetic-metering device with a receiving device, which has an inlet opening for a coupling piece or a closing piece. An essentially rigid guide lever is provided in the connection area between the receiving device and the closing piece. A hinge connection is provided which makes possible an axial displaceability of the guide lever within the inlet opening and a rotary movement of the guide lever outside the inlet opening.

5 Claims, 2 Drawing Sheets

SAFETY FILLING DEVICE FOR ANESTHETIC EVAPORATORS

FIELD OF THE INVENTION

The present invention pertains to a safety filling device for an anesthetic evaporator and more particularly to a safety filling device for filling a liquid anesthetic into a reservoir of an anesthetic-metering device, the metering device having a receiving device, which has an inlet opening for a coupling piece or a closing piece, wherein channels, which are located within the said inlet opening in a resting position, are closed for filing by the closing piece.

BACKGROUND OF THE INVENTION

A safety filling device for filling a liquid anesthetic into a filing space of an anesthetic evaporator, in which the filling is performed by means of a coupling piece that can be pushed into an inlet opening of the safety filling device, has been known from DE 41 06 906 A1. The coupling piece is connected to a stock bottle containing the liquid anesthetic. After the anesthetic evaporator has been filled, the inlet opening is closed with a closing piece, and a preferred position in relation to the inlet opening is to be maintained for inserting the closing piece. The closing piece inserted into the inlet opening is fixed within the inlet opening by means of a tightening device and is pressed against a seal located there.

The drawback of the prior-art safety filling device is that when the closing piece is inserted into the inlet opening, the preferred position of the closing piece in relation to the inlet opening must first be determined, e.g., by associating recesses present in the closing piece with corresponding projections in the inlet opening. In addition, there is a risk that the closing piece is lost during filling, and the anesthetic evaporator can no longer be used thereafter, because the filling and ventilating channels present in the inlet opening can no longer be closed.

SUMMARY AND OBJECTS OF THE INVENTION

The primary object of the present invention is to improve the arrangement of the closing piece at the safety filling device.

According to the invention, a safety filling device is provided for filling a liquid anesthetic into a reservoir of an anesthetic-metering device. The anesthetic-metering device is provided with a receiving device, which has a said inlet opening for a coupling piece or a closing piece. The channels, which are located within the inlet opening in a resting position, are closed for filling by the closing piece. An essentially rigid guide lever is provided in the connection area between the receiving device and the closing piece. A hinge connection, which makes possible an axial displaceability of the guide lever within the inlet opening and a rotary movement of the guide lever outside the said inlet opening, is provided.

The advantage of the present invention is essentially that due to the arrangement of the closing piece above the guide lever and the hinge connection at the receiving device, the closing piece always retains a preferred position in relation to the inlet opening during pulling out of the inlet opening, and it is captively connected to the receiving device. The preferred position of the closing piece in relation to the inlet opening is achieved such that the closing piece is axially displaceable within the inlet opening and can be pivoted out of the inlet opening outside the inlet opening around an axis of rotation directed at right angles to the longitudinal axis of the inlet opening.

The hinge connection of the guide lever opposite the receiving device advantageously comprises a groove extending along the inlet opening with a bolt, which is axially displaceable in it and is connected to the free end of the guide lever. The groove is arranged in a slot-like recess, which extends under a contact surface of the inlet opening and is open toward the contact surface. With the closing piece pulled out of the inlet opening, the guide lever can be pivoted around the bolt.

A spring pretensioning the closing piece in its resting position in the ejection direction is advantageously provided between the receiving device and the closing piece. The spring is preferably arranged at a rear stop surface of the inlet opening. The closing piece is pushed out of the inlet opening by a certain amount by the spring during the loosening of a tightening device, as a result of which it can be pulled out of the inlet opening in a simpler manner.

In addition, a closing piece that was not properly tightened is pushed by the spring into the field of vision of the user, as a result of which the error can be immediately recognized and corrected.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
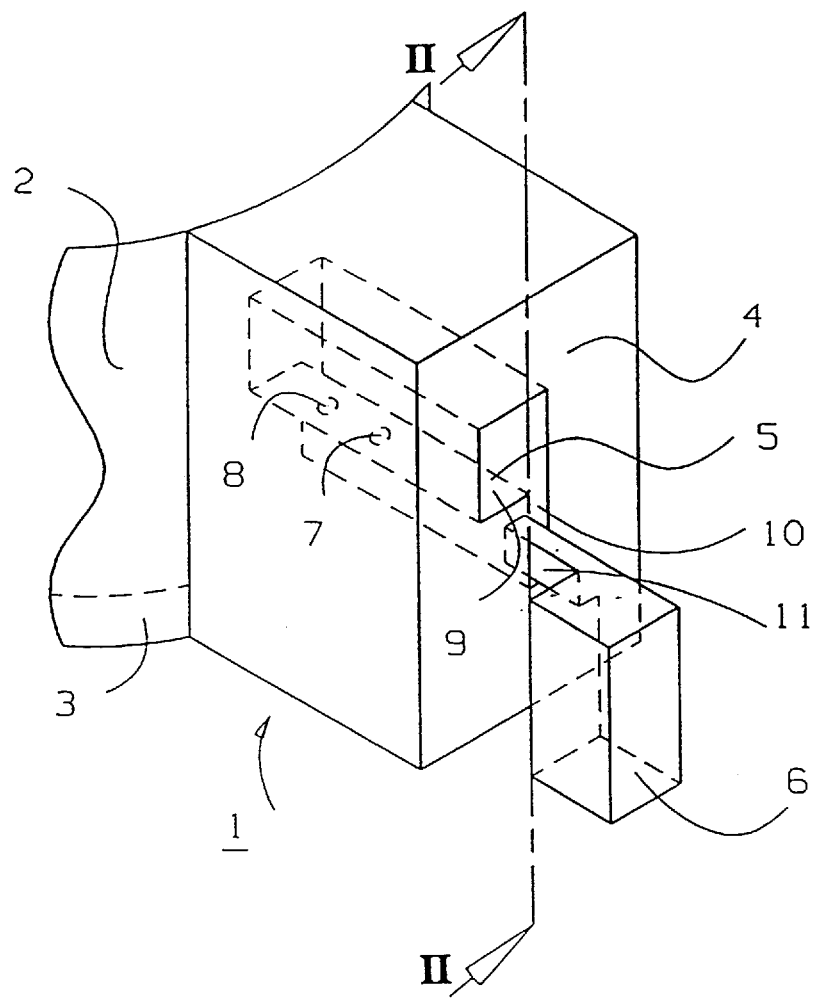
FIG. 1 is a perspective view of a safety filling device.

Referring to the drawings in particular, FIG. 1 shows a perspective view of a safety filling device 1, which is connected to an anesthetic evaporator 2, which is shown only partially in FIG. 1. The anesthetic evaporator 2 has a reservoir 3 for liquid anesthetic in its lower part. The safety filling device 1 comprises a receiving device 4 with an inlet opening 5 and with a closing piece 6 that can be pushed into the inlet opening 5. A filling channel 7 and a ventilating channel 8, which are connected to the reservoir 3 within the anesthetic evaporator 2, are arranged within the inlet opening 5. The closing piece 6 is in a so-called operating position in the position shown in FIG. 1, in which a coupling piece, not shown in FIG. 1, can be pushed into the inlet opening 5. A filling channel and a ventilating channel, which are connected to the channels 7, 8 within the inlet opening 5, are also present within the coupling piece.

Figure 2:
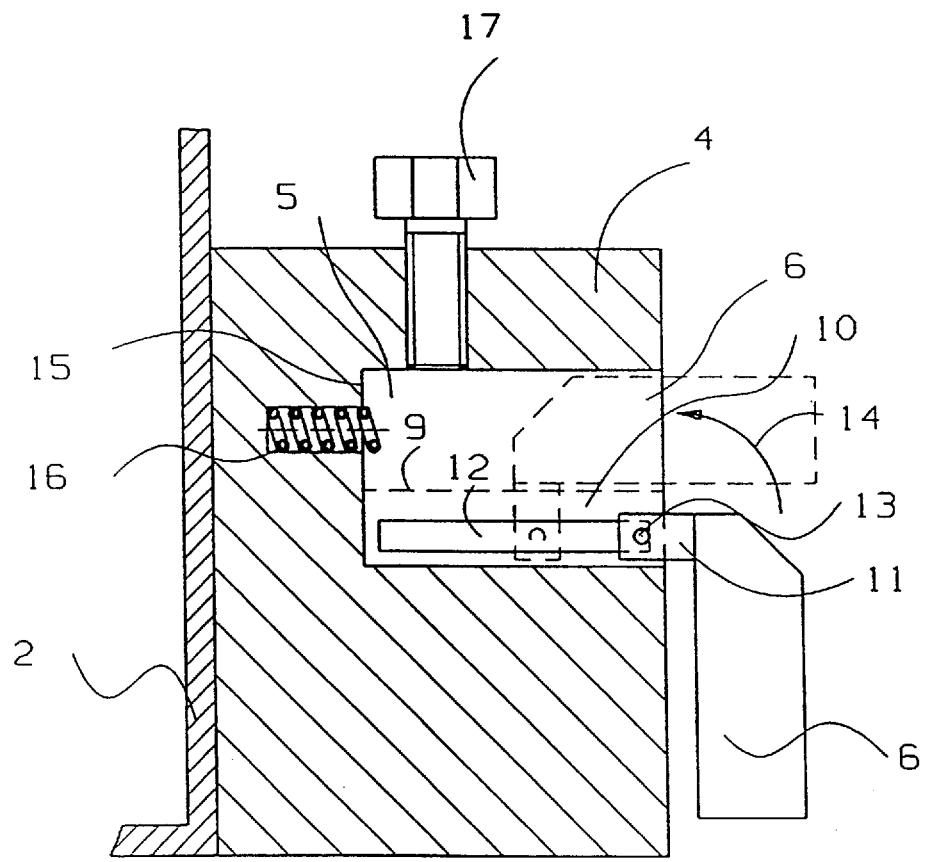
FIG. 2 is a sectional view taken along line II—II of the safety filling device according to FIG. 1.

FIG. 2 shows a sectional view of the safety filling device 1 along a section line II—II. Identical components are designated by the same reference numbers as in FIG. 1. A recess 10 (FIG. 1) originating from a lower contact surface 9 is located within the inlet opening 5 (FIG. 1) for receiving a guide lever 11, which is connected to the closing piece 6. The guide lever 11 is connected to the rear end of the closing piece 6 and forms a right angle with the closing piece 6. The contact surface 9, FIG. 1, is illustrated by a broken line in FIG. 2 for greater clarity, even though it is not visible in this view. A groove 12 extending along the inlet opening 5 is provided within the recess 10, and a bolt 13, which is connected to the end of the guide lever 11 and is axially displaceable within the inlet opening 5, is accommodated in the said groove 12. A corresponding groove is also located in the opposite wall part of the recess 10.

The groove 12 is shown enlarged in FIG. 2 for the sake of greater clarity. The combination of the bolt 13 and the groove 12 forms a hinge connection of the guide lever 11 with the receiving device 4. Axial displaceability of the closing piece 6 within the inlet opening 5 and rotatability of the closing piece 6 outside the inlet opening 5 are achieved due to the hinge connection.

To close the inlet opening 5, the closing piece 6 is pivoted around the bolt 13 along the arrow 14, and then displaced along the groove 12 until the closing piece 6 comes into contact with a stop 15 and a spring 16. In this position, the closing piece 6 is in the so-called resting position, in which the filling channel 7 and the ventilating channel 8 (FIG. 1) are closed. The closing piece 6 is tensioned against the contact surface 9 by means of a knurled screw 17 in the resting position. The knurled screw 17 is not shown in FIG. 1 for the sake of greater clarity. The spring 16 is slightly pretensioned in the resting position of the closing piece 6, so that the closing piece 6 is pushed out of the inlet opening 5 by a certain amount during the loosening of the knurled screw 17, as a result of which it can be pushed out of the inlet opening 5 more easily. The closing piece 6 partially pushed into the inlet opening 5 is shown by broken lines in FIG. 2. Another advantage of the spring 16 is that a closing piece 6 not properly tightened by means of the knurled screw 17 is pushed by the spring into the field of vision of the user, not shown in FIG. 2, as a result of which the error can be immediately recognized and corrected.

While specific embodiments of the invention have been shown and described in detail to illustrate the application of the principles of the invention, it will be understood that the invention may be embodied otherwise without departing from such principles.

What is claimed is:

1. A safety filling device for filling a liquid anesthetic into a reservoir of an anesthetic-metering device, comprising:

a receiving device which has an inlet opening, said receiving device having channels, which are located within said inlet opening;

a closing member including a closing piece wherein said channels, which are located within said inlet opening are closed for filling by said closing member;

an essentially rigid guide lever provided in a connection area between said receiving device and said closing member; and a hinge connection for axially displacing said guide lever within said inlet opening and for a rotary movement of the said guide lever outside the said inlet opening.

2. A device in accordance with claim 1, wherein said hinge connection comprises a groove extending along the said inlet opening and a bolt, which is axially displaceable within the said groove and is connected to one end of said guide lever.

3. A device in accordance with claim 2, wherein said groove is arranged in a slot-like recess which extends under a contact surface of said inlet opening and is open toward said contact surface.

4. A device in accordance with one of the claim 1, further comprising a spring pretensioning said closing piece in a resting position in an ejection direction is provided between said receiving device and said closing piece.

5. A device in accordance with claim 4, wherein said spring is arranged in an area of said rear stop surface of said inlet opening.

* * * * *